(12) United States Patent
Govari et al.

(10) Patent No.: US 10,765,475 B2
(45) Date of Patent: Sep. 8, 2020

(54) ALL-IN-ONE SPIRAL CATHETER

(71) Applicant: Biosense Webster (Israel) Ltd., Yokneam (IL)

(72) Inventors: Assaf Govari, Haifa (IL); Christopher Thomas Beeckler, Brea, CA (US); Joseph Thomas Keyes, Glendora, CA (US); Kevin Justin Herrera, West Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 263 days.

(21) Appl. No.: 15/798,821

(22) Filed: Oct. 31, 2017

(65) Prior Publication Data

US 2019/0125437 A1    May 2, 2019

(51) Int. Cl.
| | | |
|---|---|---|
| *A61B 18/14* | (2006.01) | |
| *A61M 25/00* | (2006.01) | |
| *A61B 5/042* | (2006.01) | |
| *A61B 5/00* | (2006.01) | |
| *A61B 18/00* | (2006.01) | |
| *A61B 17/00* | (2006.01) | |

(52) U.S. Cl.
CPC ........ *A61B 18/1492* (2013.01); *A61B 5/0422* (2013.01); *A61B 5/6852* (2013.01); *A61B 5/6856* (2013.01); *A61M 25/005* (2013.01); *A61B 5/6851* (2013.01); *A61B 2017/00243* (2013.01); *A61B 2017/00292* (2013.01); *A61B 2018/00351* (2013.01)

(58) Field of Classification Search
CPC .......... A61B 18/42; A61B 2018/00351; A61B 2017/00243; A61B 2017/00292; A61B 5/6851; A61B 5/6852; A61B 5/6856; A61M 25/005

See application file for complete search history.

(56) References Cited

U.S. PATENT DOCUMENTS

| | | | | |
|---|---|---|---|---|
| 5,016,808 A | * | 5/1991 | Heil, Jr. ................. | A61N 1/056 228/176 |
| 5,156,151 A | * | 10/1992 | Imran .................... | A61N 1/056 600/375 |
| 5,462,545 A | * | 10/1995 | Wang ................. | A61B 18/1492 600/373 |
| 5,546,951 A | | 8/1996 | Ben Haim | |

(Continued)

FOREIGN PATENT DOCUMENTS

| | | |
|---|---|---|
| DE | 4025369 A1 | 2/1991 |
| EP | 2269505 A1 | 1/2011 |

(Continued)

OTHER PUBLICATIONS

International Search Report and Written Opinion dated Jan. 16, 2019 for International Application No. PCT/US2018/055124, 17 pages.

*Primary Examiner* — Michael F Peffley
(74) *Attorney, Agent, or Firm* — Frost Brown Todd LLC (57) ABSTRACT

Medical catheterization is carried out by introducing a catheter into a heart, sliding the catheter through a sheath that encloses a multi-electrode probe into a chamber of the heart. The sheath is retracted to expose the probe. As the sheath is retracted the exposed probe expands into a spiral configuration, and the electrodes contact the endocardial surface of the chamber at multiple contact points.

13 Claims, 5 Drawing Sheets

(56) References Cited

U.S. PATENT DOCUMENTS

| | | | |
|---|---|---|---|
| 5,680,860 A * | 10/1997 | Imran | A61B 18/1492 600/374 |
| 5,738,096 A | 4/1998 | Ben Haim | |
| 5,873,865 A | 2/1999 | Horzewski | |
| 6,226,542 B1 | 5/2001 | Reisfeld | |
| 6,301,496 B1 | 10/2001 | Reisfeld | |
| 6,690,963 B2 | 2/2004 | Ben Haim | |
| 6,711,444 B2 * | 3/2004 | Koblish | A61B 18/1492 600/373 |
| 6,814,733 B2 | 11/2004 | Schwartz | |
| 6,892,091 B1 | 5/2005 | Ben Haim | |
| 6,997,924 B2 | 2/2006 | Schwartz | |
| 7,156,816 B2 | 1/2007 | Schwartz | |
| 7,536,218 B2 | 5/2009 | Govari | |
| 7,756,576 B2 | 7/2010 | Levin | |
| 8,478,383 B2 | 7/2013 | Bar-Tal | |
| 8,834,464 B2 * | 9/2014 | Stewart | A61B 18/1492 600/372 |
| 2002/0072740 A1 | 6/2002 | Chandrasekaran et al. | |
| 2003/0176758 A1 | 9/2003 | Nakano | |
| 2010/0114022 A1 | 5/2010 | Hirszowicz | |
| 2012/0116382 A1 | 5/2012 | Ku et al. | |
| 2012/0197246 A1 | 8/2012 | Mauch | |
| 2012/0245520 A1 | 9/2012 | Kelly | |

FOREIGN PATENT DOCUMENTS

| | | |
|---|---|---|
| EP | 2859861 A1 | 4/2015 |
| WO | WO 96/05768 A1 | 2/1996 |

* cited by examiner

ALL-IN-ONE SPIRAL CATHETER

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to transferring non-mechanical forms of energy to or from the body. More particularly, this invention relates to transmission and reception of electrical signals of the heart for diagnostic and therapeutic purposes.

2. Description of the Related Art

Cardiac arrhythmias such as atrial fibrillation are an important cause of morbidity and death. Commonly assigned U.S. Pat. Nos. 5,546,951, and 6,690,963, both issued to Ben Haim, and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. Nos. 6,226,542, and 6,301,496, both issued to Reisfeld, which are incorporated herein by reference.

As indicated in these patents, location and electrical activity are typically initially measured on about 10 to about 20 points on the interior surface of the heart. These data points are then generally sufficient to generate a preliminary reconstruction or map of the cardiac surface. The preliminary map is often combined with data taken at additional points in order to generate a more comprehensive map of the heart's electrical activity. Indeed, in clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, which is incorporated herein by reference, maps depicting such motion characteristics may be constructed when the trajectory information is sampled at a sufficient number of points in the heart.

Electrical activity at a point in the heart is typically measured by advancing a catheter containing an electrical sensor at or near its distal tip to that point in the heart, contacting the tissue with the sensor and acquiring data at that point. One drawback with mapping a cardiac chamber using a catheter containing only a single, distal tip electrode is the long period of time required to accumulate data on a point-by-point basis over the requisite number of points required for a detailed map of the chamber as a whole. Accordingly, multiple-electrode catheters have been developed to simultaneously measure electrical activity, such as local activation times (LAT) at multiple sampled points in the heart chamber.

Procedures for treating arrhythmia include disrupting the areas causing the arrhythmia by ablation, as well as disrupting the conducting pathway for such signals. Ablation of body tissue using electrical energy is known in the art. The ablation is typically performed by applying alternating currents, for example radiofrequency energy, to one or more ablation electrodes, at a sufficient power to destroy target tissue. Typically, the electrodes are mounted on the distal tip or portion of an invasive probe or catheter, which is inserted into a subject. The distal tip may be tracked in a number of different ways known in the art, for example by measuring magnetic fields generated at the distal tip by coils external to the subject.

SUMMARY OF THE INVENTION

In the absence of a system in which a catheter, once it is fixed in position in a heart chamber, can be used to analyze the electropotentials of a heart chamber and then be used to form a lesion on substantially any selected portion of the chamber wall an ablation procedure needs to be performed in a number of distinct steps. Each of the steps requires insertion and withdrawal of a suitable catheter into the heart. Requiring more than one catheter insertion and removal extends the time needed to complete the ablation procedure.

Embodiments of the invention provide a catheter having an "all-in-one" distal end. Once the distal end has been inserted into a selected heart chamber, it is able to map the electropotentials of the entire heart chamber, and to ablate any selected portion of the wall of the chamber.

The distal end of the catheter is a flexible insulated tube upon which are formed multiple relatively large electrodes, suitable for use as ablation electrodes, together with smaller microelectrodes, which may be used to take bioelectric readings or inject electropotentials. The microelectrodes may also be used as mapping electrodes. The ablation electrodes and the microelectrodes are individually addressable.

The insulated tube may be terminated by a movable rotator and by a holding element. Initially the tube is effectively straight and is inserted into a selected heart chamber so that the holding element provides purchase, i.e., an effective holding contact to the wall of the chamber, thereby fixing the distal end of the tube in place. The rotator enables the straight tube to rotate about a longitudinal axis, whereupon the tube expands into a three-dimensional spiral, and presses against the walls of the chamber. The rotator is then detached and withdrawn proximally, When the rotator is completely withdrawn the tube is fully deployed.

Typically, with a fully deployed spiral, measurements from the microelectrodes are used to map the electropotentials of the chamber. A physician is then able to use the map to decide where to ablate in the chamber, and is then able to select the individual ablation electrodes according to the location selected for ablation.

There is provided according to embodiments of the invention a method of medical catheterization, which is carried out by introducing a multi-electrode catheter into a heart, sliding the catheter through a sheath into a chamber of the heart, retracting the sheath to expose the catheter, while retracting the sheath expanding the exposed catheter into a spiral configuration, and contacting the expanding exposed catheter to an endocardial surface of the chamber at multiple contact points.

According to one aspect of the method, retracting the sheath is performed while holding the catheter in position.

A further aspect of the method includes advancing the catheter while retracting the sheath.

The catheter may include a flexible, electrically insulated tube, a plurality of ablation electrodes disposed on the external surface of the tube in electrical isolation from one another, and a plurality of microelectrodes in electrical isolation from one another and from the ablation electrodes, An aspect of the method includes reading bioelectrical signals from the heart with the microelectrodes, and conducting electrical energy through selected ablation electrodes to produce a lesion in the chamber of the heart.

The catheter may include a holding element. An aspect of the method includes contacting the holding element to a wall of the heart to provide purchase for the catheter on the wall, and while retracting the sheath, rotating the catheter with respect to the sheath.

According to one aspect of the method, the catheter has a shape memory that urges the probe to form spiral loops.

A further aspect of the method includes taking bioelectric readings from selected ones of the microelectrodes and preparing a map of electrical activity in the heart based on the readings.

Yet another aspect of the method includes injecting electropotentials into the heart through selected ones of the microelectrodes.

Another aspect of the method a ring is disposed about a distal portion of a guide wire. The ring is freely slidable and rotatable on the guide wire, and connected to the distal end of the probe for insertion therewith into the chamber. An aspect of the method includes rotating the catheter about the guide wire while retracting the sheath.

According to yet another aspect of the method, the guide wire has a proximal stop and a distal stop for limiting sliding motion of the ring on the guide wire.

There is further provided according to embodiments of the invention an apparatus for medical catheterization, including an assembly adapted for introduction into a heart, and a catheter slidable through the assembly into a chamber of the heart. The catheter includes a sheath, and comprises a multi-electrode probe movable through the sheath in a compact configuration. The probe has a shape memory that urges the probe to assume an expanded spiral configuration when advanced beyond the sheath into the chamber.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Overview.

Figure 1:
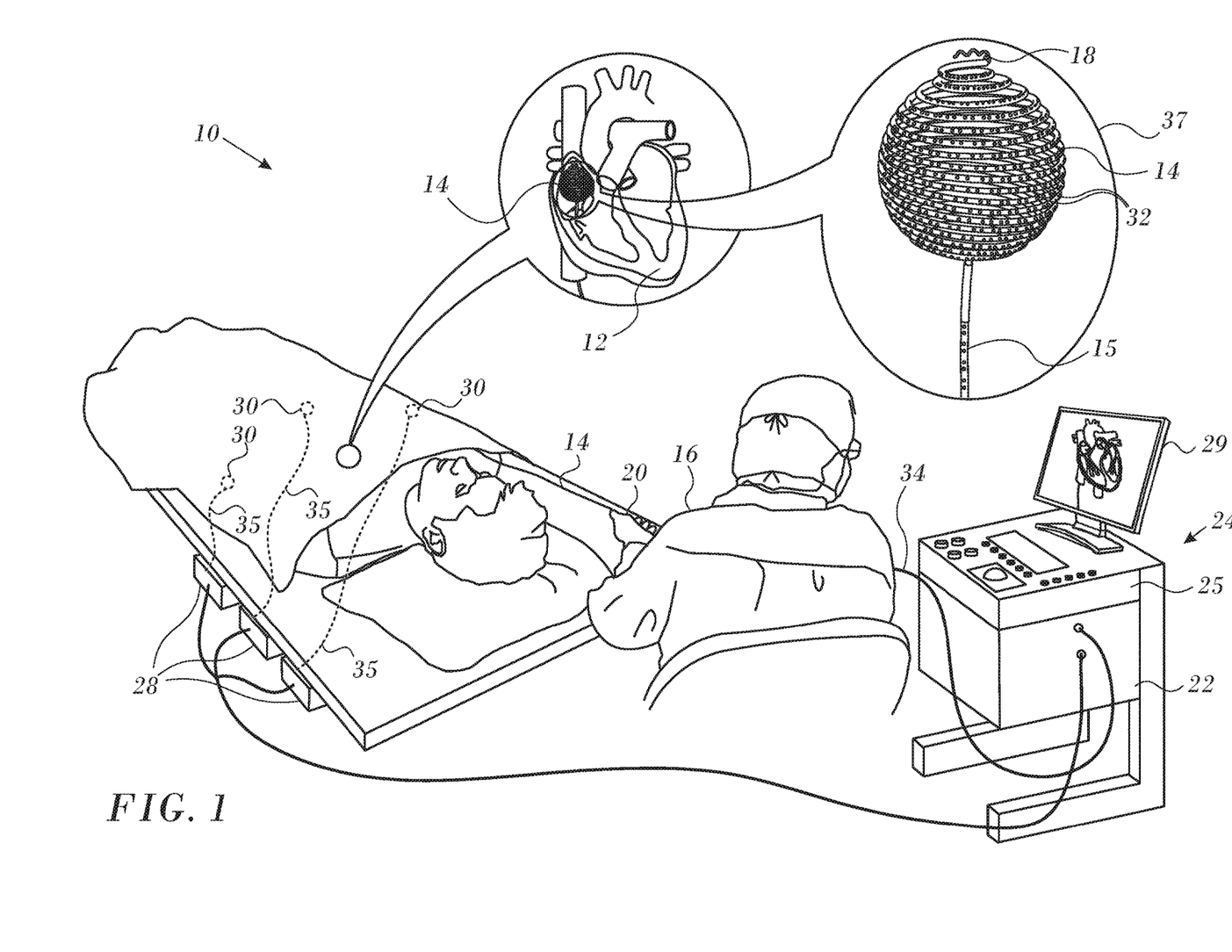
FIG. 1 is a pictorial illustration of a system for performing catheterization procedures on a heart, in accordance with a disclosed embodiment of the invention.

Turning now to the drawings, reference is initially made to FIG. 1, which is a pictorial illustration of a system 10 for performing diagnostic and therapeutic procedures on a heart 12 of a living subject, which is constructed and operative in accordance with a disclosed embodiment of the invention. The system comprises a multi-electrode catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301, 496, and in commonly assigned U.S. Pat. No. 6,892,091, whose disclosures are herein incorporated by reference.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic. One commercial product embodying elements of the system 10 is available as the CARTO® 3 System, available from Biosense Webster, Inc., 3333 Diamond Canyon Road, Diamond Bar, Calif. 91765.

This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically above 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains one or more position sensors (not shown) that provide signals to a processor 22, located in a console 24. The processor 22 may fulfill several processing functions as described below. As explained below, the catheter 14 is inserted by the operator 16 into the heart 12 through a sheath 15, typically via the inferior vena cava.

The catheter 14 has a spiral configuration as shown in balloon 37 with multiple electrodes 32, which are used for sensing and ablation as described below. Once the catheter is located in the heart, by constructing a current position map, the location of each of the electrodes 32 in the heart becomes known. One method for generation of a position map is described in commonly assigned U.S. Pat. No. 8,478,383 to Bar-Tal et al., which is herein incorporated by reference.

Electrical signals can be conveyed to and from the heart 12 from the electrodes 32 located at or near the distal tip 18 of the catheter 14 via cable 34 to the console 24. Pacing signals and other control signals may be conveyed from the console 24 through the cable 34 and the electrodes 32 to the heart 12.

Wire connections 35 link the console 24 with body surface electrodes 30 and other components of a positioning sub-system for measuring location and orientation coordinates of the catheter 14. The processor 22, or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. Temperature sensor (not shown), typically a thermocouple or thermistor, may be mounted near the electrodes 32 that are used for ablation.

The console 24 typically contains one or more ablation power generators 25. The catheter 14 may be adapted to conduct ablative energy to the heart using any known ablation technique, e.g., radiofrequency energy, DC electrical energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. A suitable positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes as described in further detail below.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally applied reference patch attached to the exterior of the subject's body, or on an internally-placed catheter, which is inserted into the heart 12 and maintained in a fixed position relative to the heart 12. The system 10 may receive image data from an external imaging modality, such as an MRI unit or the like and includes image processors that can be incorporated in or invoked by the processor 22 for generating and displaying images.

First Embodiment

Figure 2:
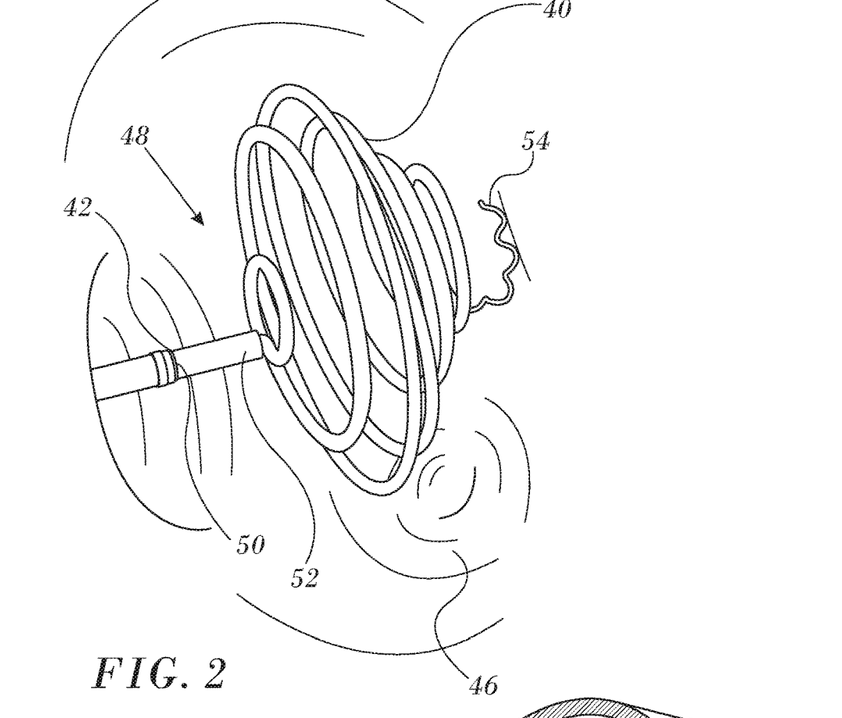
FIG. 2 is a view of an assembly in the distal portion of a catheter in accordance with an embodiment of the invention.

Reference is now made to FIG. 2, which is a view of an assembly in the distal portion of a catheter 40 in accordance with an embodiment of the invention. The distal tip of an outer sheath 42 is within the left atrium of the heart 12 (FIG. 1). Pulmonary vein ostium 46 is visible. A spiral assembly 48 is in the process of deployment into the atrium through lumen 50. An inner sheath 52 can be extended beyond the sheath 42. The distal portion of catheter 40 and the inner sheath 52 are advanced through the sheath 42 and can rotate within the inner sheath 52, generally about the longitudinal axis of the sheath 42.

As the catheter 40 advances it eventually encounters a wall of the atrium, and is held in place against the wall by a holding element 54. The holding element 54 provides a purchase, i.e., an effective holding pressure against with the wall, without being fixedly joined or interlocked with the wall. Deployment of the assembly 48 is then completed by retracting the inner sheath 52 while allowing the catheter 40 to rotate. A shape memory in the catheter 40 causes multiple points of the catheter 40 to contact the wall as shown in FIG. 1. The catheter 40 may be advanced further through inner sheath 52 to provide more loops in contact with the wall.

Figure 3:
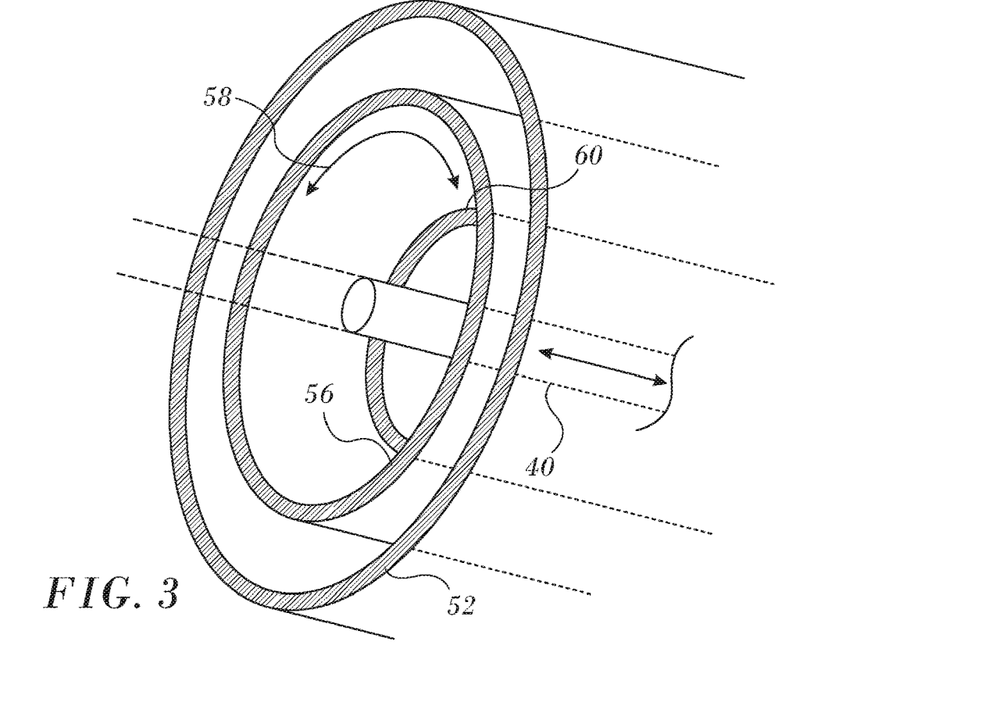
FIG. 3 is a schematic view of the distal portion of a catheter in accordance with an embodiment of the invention.

Reference is now made to FIG. 3, which is a detailed schematic view of the distal end of the inner sheath 52 during deployment of catheter 40 in accordance with an embodiment of the invention. The catheter 40 is advanced through the inner sheath 52 and through a bushing 56. The bushing 56 is freely rotatable within the inner sheath 52 as indicated by a double-headed arrow 58. The catheter 40 is loosely held against the interior wall of the bushing 56 by a girdle 60, so that the catheter 40 can slide through the girdle 60. The bushing 56 rotates about the axis of the girdle 60 as the catheter 40 deploys and unfurls. The girdle 60 prevents the catheter 40 from kinking, bunching or knotting at the end of the inner sheath 52 when the catheter 40 is being retracted into the inner sheath 52.

Second Embodiment

Figure 4:
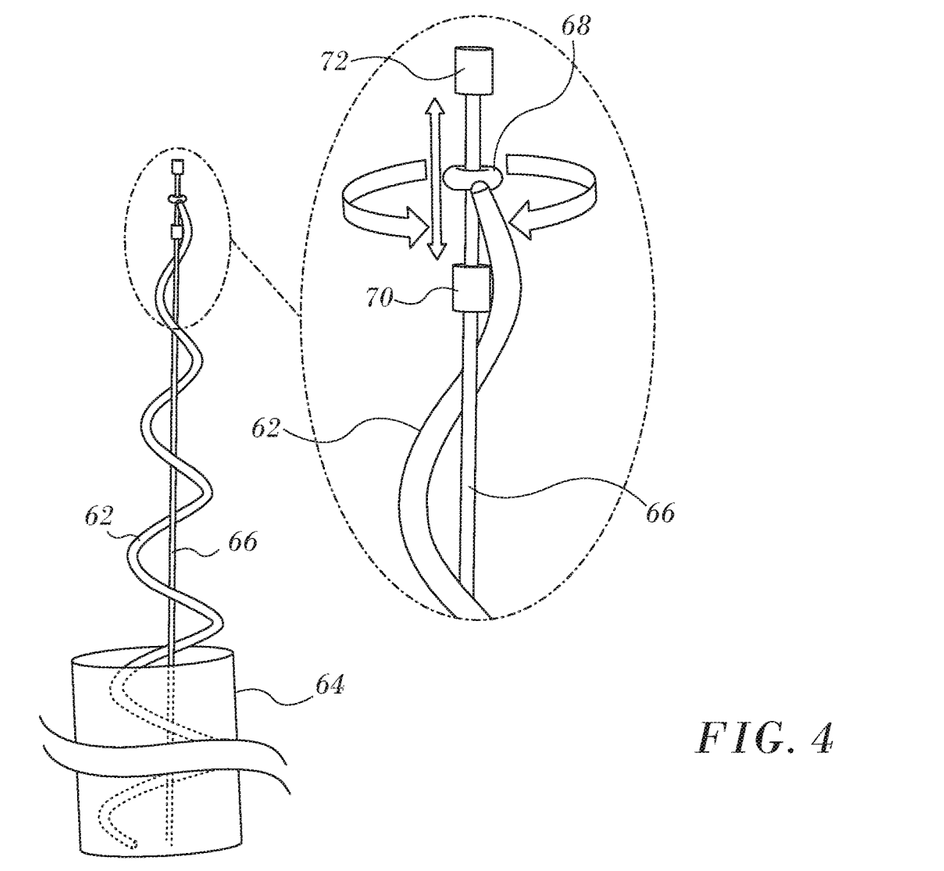
FIG. 4 is a schematic view of the distal portion of a catheter in accordance with an alternate embodiment of the invention.

Reference is now made to FIG. 4, which is a schematic view of the distal portion of a catheter 62 in accordance with an alternate embodiment of the invention. The catheter 62 is advanced beyond the end of a sheath 64 using a guide wire 66. The end portion of the guide wire 66 is loosely encircled by a ring 68. The ring 68 is freely slidable and rotatable on the guide wire 66. The tip of the catheter 62 is attached to the ring 68, so that the catheter 62 can rotate about the guide wire 66 as well as slide axially. Axial motion of the ring 68 and hence the distal end of catheter 62 along the guide wire 66 is constrained by proximal stop 70 and distal stop 72, one on either side of the ring 68, so that the ring 68 is disposed between the stops 70, 72. When the sheath 64 is retracted, and the catheter 62 advances progressively beyond the end of the sheath 64, its shape memory causes it to assume the spiral configuration illustrated by FIG. 1 and FIG. 2. Torque exerted by the catheter 62 as it expands forces the catheter 62 to rotate about the guide wire 66. The operator may rotate the catheter 62 while the sheath 64 is being retracted.

Figure 5:
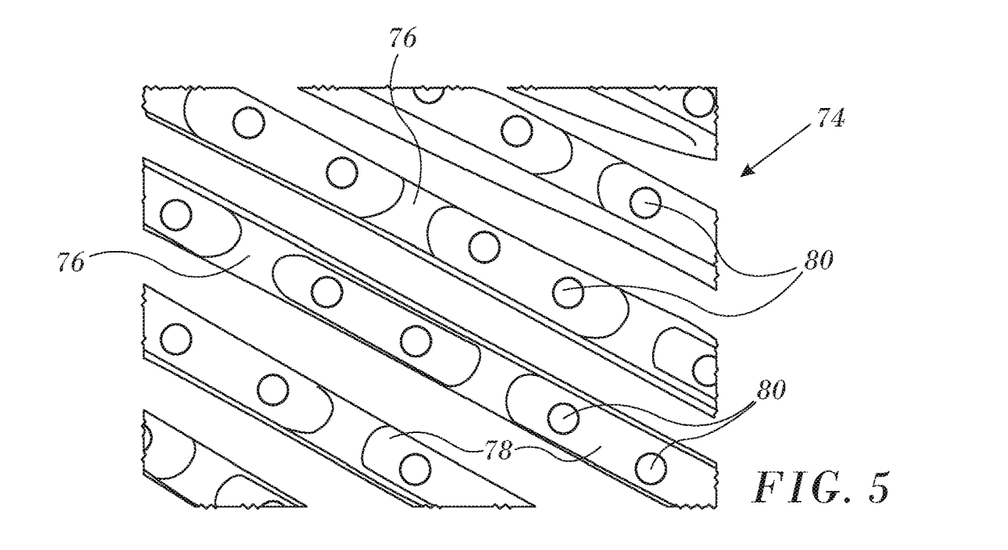
FIG. 5 is a detailed view of a portion of the catheter shown in FIG. 2 in accordance with an embodiment of the invention.

Reference is now made to FIG. 5, which is a detailed view of a portion of a catheter 74 in accordance with an embodiment of the invention. The catheter 74 is a flexible electrically insulated tube 76 made of polyurethane, polyether block amide, or other suitable polymer. Multiple electrodes 78, used for ablation, are disposed on the surface of the tube 76. In some embodiments, the tube 76 may have a shape memory spine inside, e.g., nitinol, such that when distally anchored by the holding element 54, the catheter 74 is tends to configure itself as a series of spiral loops, as shown, e.g., in FIG. 4.

Microelectrodes 80 are associated with the electrodes 78. Indeed, the electrodes 78 and microelectrodes 80 may be manufactured as integral units, electrically isolated from one another, preferably with features that minimize parasitic capacitance. Such integral units can be constructed, mutatis mutandis, according to the teachings of commonly assigned U.S. Patent Application Publication No. 20160100878, entitled Effective Parasitic Capacitance Minimization for Micro Ablation Electrode, the disclosure of which is hereby incorporated by reference.

Referring again to FIG. 3, after the catheter 40 is advanced and held in place, and thereafter the inner sheath 52 withdrawn, Aided by the bushing 56, friction opposing rotation of the catheter 40 between the holding element 54 and the heart wall is weak relative to the friction within the sheath 64 (FIG. 4).

The shape memory of the catheter 40 causes the catheter 40 to exert torsion about the axis of the inner sheath 52, which is transmitted to the bushing 56 by the girdle 60. The bushing 56 is rotatable within the inner sheath 52. Consequently, the catheter 40 is able to rotate about the axis of the inner sheath 52.

The electrodes 78 and microelectrodes 80 are connected to the console 24 (FIG. 1) by conductors (not shown), and are individually addressable, i.e., electrical voltages or currents can be transmitted or sensed via selected ones of the electrodes 78 and microelectrodes 80. The microelectrodes 80 are typically used for electrically mapping the heart, as noted above. Alternatively, the microelectrodes 80 may be used to inject electrical potentials as taught in commonly assigned U.S. Pat. No. 9,370,312, which is herein incorporated by reference.

Deployment.

Figure 6:
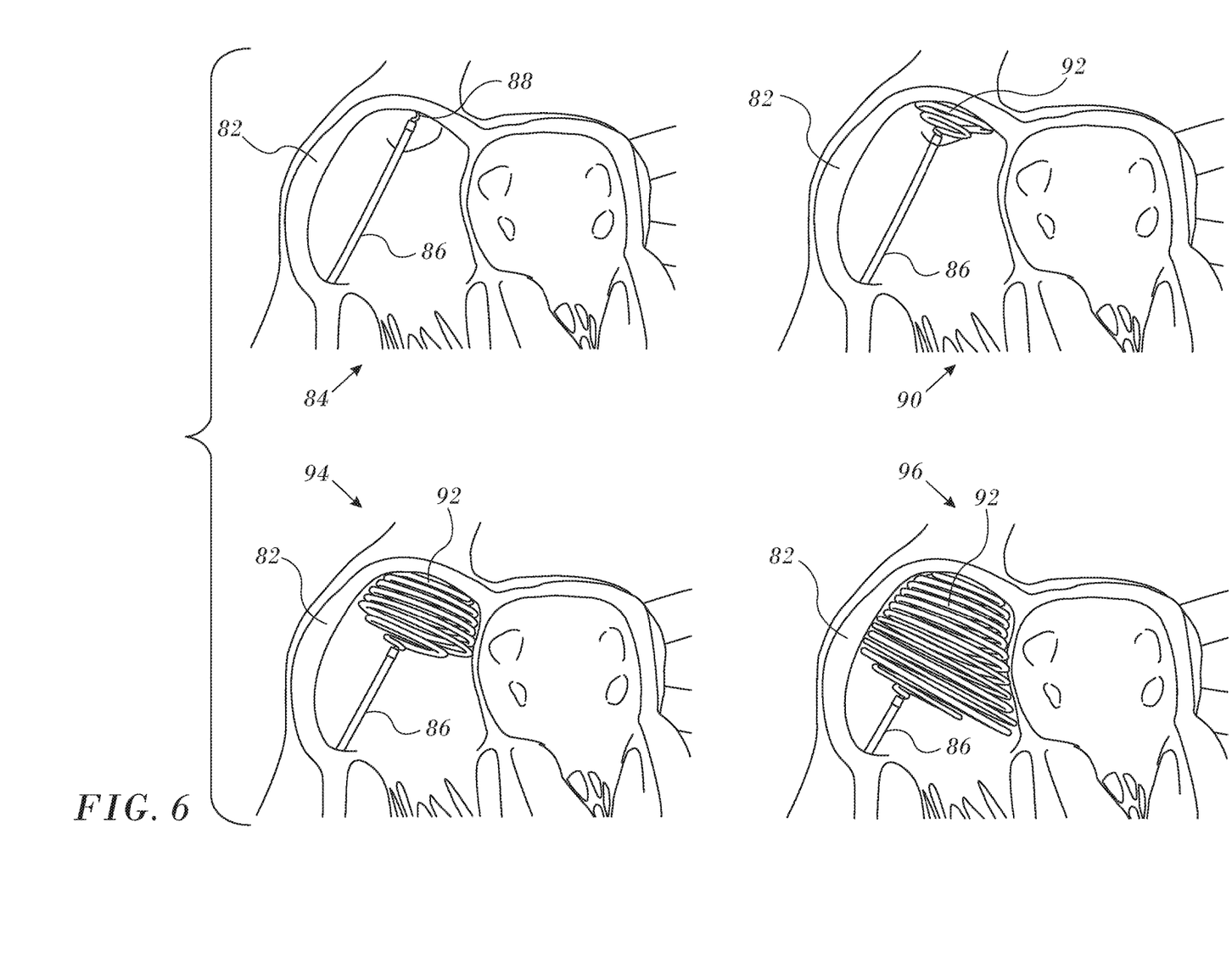
FIG. 6 is a set of schematic illustrations of a heart illustrating deployment of a catheter through a sheath into the right atrium in accordance with an embodiment of the invention and FIG. 7 is a schematic cutaway view of a heart with the assembly shown in FIG. 2 deployed in accordance with an embodiment of the invention.

Reference is now made to FIG. 6, which is a set of schematic views illustrating deployment of a catheter through a sheath into right atrium 82 in accordance with an embodiment of the invention. In frame 84 sheath 86 has been navigated via the inferior vena cava to a position in the superior aspect of the right atrium. A portion of holding element 88 protrudes through the end of the sheath 86.

In frame 90 the sheath 86 has begun to be withdrawn relative to catheter body 92 while holding the catheter body 92 in place using a manipulation tool (not shown) in the proximal portion of the catheter. The shape memory element of the catheter body 92 causes the catheter body 92 to assume a spiral configuration. Withdrawal of the sheath 86 can be accompanied by additional advancement of the catheter body 92, which facilitates full deployment of the catheter. The catheter is considerably longer than the dimension of the cardiac chamber, so that simply retracting the sheath 86 may not necessarily permit all the loops to expand and contact the wall of the cardiac chamber In frame 94 withdrawal of the sheath 86 continues, and the catheter body 92 occupies approximately ⅓ of the right atrium. In frame 96 the process is progressed such that the catheter body 92 occupies approximately ¾ of the right atrium. As before, withdrawal of the sheath 86 can be accompanied by additional advancement of the catheter body 92.

Figure 7:
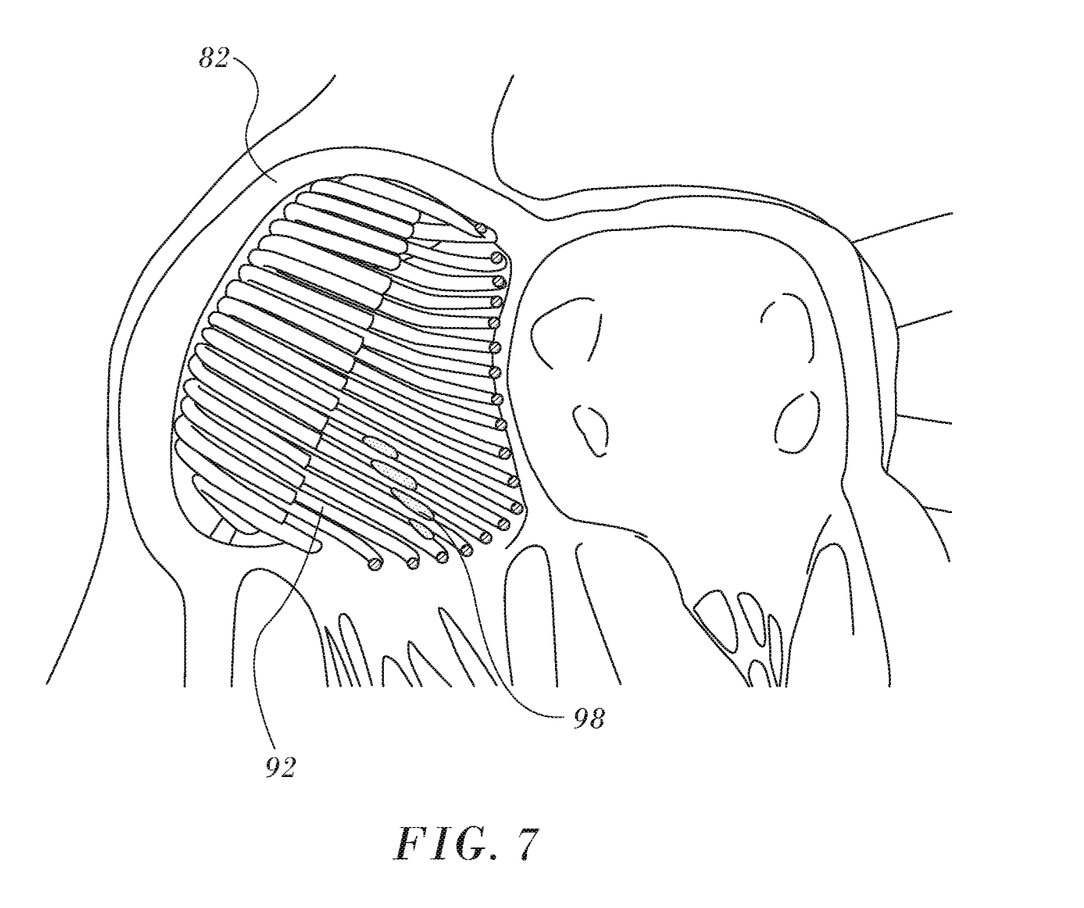

Reference is now made to FIG. 7, which is a schematic cutaway view of a heart with the catheter body 92 fully deployed in right atrium 82 in accordance with an embodiment of the invention. Most areas of the endocardial surface have some contact with the spiral loops of the catheter body 92. An area 98 represents a lesion created by selectively energizing the ablation electrodes that contact the area 98.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method of medical catheterization, comprising the steps of:
   introducing a multi-electrode catheter into a heart, sliding the catheter into a chamber of the heart through a sheath;
   retracting the sheath to expose the catheter; while retracting the sheath expanding the exposed catheter into a spiral configuration;
   contacting the expanded catheter to an endocardial surface of the chamber at multiple contact points,
   disposing a ring about a distal portion of a guide wire, the ring being freely slidable and rotatable on the guide wire;
   connecting the ring to a distal end of the catheter for insertion therewith into the chamber; and
   while retracting the sheath, rotating the catheter about the guide wire.

2. The method according to claim 1, wherein retracting the sheath is performed while holding the catheter in position.

3. The method according to claim 1, further comprising advancing the catheter while retracting the sheath.

4. The method according to claim 1, wherein the catheter comprises:
a flexible, electrically insulated tube having an external surface; a plurality of ablation electrodes disposed on the external surface of the tube in electrical isolation from one another; and a plurality of microelectrodes in electrical isolation from one another and from the ablation electrodes, the method further comprising the steps of:
reading bioelectrical signals from the heart with the microelectrodes; and
conducting electrical energy through selected ones of the ablation electrodes to produce a lesion in the chamber of the heart.

5. The method according to claim 4, wherein the catheter further comprises a holding element, further comprising contacting the holding element to a wall of the heart to provide purchase for the catheter on the wall, the method further comprising the step of:
while retracting the sheath, rotating the catheter with respect to the sheath.

6. The method according to claim 4, wherein the catheter has a shape memory that urges the catheter to form spiral loops.

7. The method according to claim 4, further comprising taking bioelectric readings from selected ones of the microelectrodes and preparing a map of electrical activity in the heart based on the readings.

8. The method according to claim 4, further comprising injecting electropotentials into the heart through selected ones of the microelectrodes.

9. The method according to claim 1, wherein the guide wire has a proximal stop and a distal stop for limiting sliding motion of the ring on the guide wire.

10. An apparatus for medical catheterization, comprising:
an assembly adapted for introduction into a heart; and
a catheter slidable through the assembly into a chamber of the heart, comprising:
a sheath; and
a multi-electrode probe movable through the sheath in a compact configuration, the probe having a distal end and a shape memory that urges the probe to assume an expanded spiral configuration when advanced beyond the sheath into the chamber, wherein the assembly further comprises:
a guide wire; and
a ring disposed about a distal portion of the guide wire, the ring being freely slidable and rotatable on the guide wire, and the ring being connected to the distal end of the probe for insertion therewith into the chamber.

11. The apparatus according to claim 10, wherein the probe comprises:
a flexible, electrically insulated tube having an external surface;
a plurality of ablation electrodes disposed on the external surface of the tube in electrical isolation from one another; and
a plurality of microelectrodes in electrical isolation from one another and from the ablation electrodes.

12. The apparatus according to claim 11, wherein the probe further comprises a holding element adapted for contacting a wall of the heart.

13. The apparatus according to claim 10, wherein the guide wire has a proximal stop and a distal stop for limiting sliding motion of the ring on the guide wire.

* * * * *